(12) United States Patent
Lim

(10) Patent No.: US 7,252,673 B2
(45) Date of Patent: Aug. 7, 2007

(54) DEVICES AND METHODS FOR INSERTING SPINAL IMPLANTS

(75) Inventor: Roy Lim, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 498 days.

(21) Appl. No.: 10/659,461

(22) Filed: Sep. 10, 2003

(65) Prior Publication Data

US 2005/0055031 A1    Mar. 10, 2005

(51) Int. Cl.
A61B 17/58    (2006.01)
A61B 17/60    (2006.01)

(52) U.S. Cl. .......................................... 606/99; 606/90

(58) Field of Classification Search ................. 606/99, 606/86, 100, 90, 205, 206, 207; 623/17.11, 623/17.16
See application file for complete search history.

(56) References Cited

U.S. PATENT DOCUMENTS

| | | | |
|---|---|---|---|
| 5,431,658 A | 7/1995 | Moskovich | |
| 5,688,276 A | 11/1997 | Shaffer | |
| 5,735,842 A | 4/1998 | Krueger et al. | |
| 5,788,713 A | 8/1998 | Kubach et al. | |
| 5,947,970 A | 9/1999 | Schmelzeisen et al. | |
| 5,951,564 A * | 9/1999 | Schroder et al. | 606/100 |
| 5,957,927 A | 9/1999 | Magee et al. | |
| 6,036,692 A | 3/2000 | Burel et al. | |
| 6,113,605 A | 9/2000 | Storer | |
| 6,126,674 A * | 10/2000 | Janzen | 606/206 |
| 6,156,037 A | 12/2000 | LeHuec et al. | |
| 6,159,215 A | 12/2000 | Urbahns et al. | |
| 6,440,169 B1 | 8/2002 | Elberg et al. | |
| 6,478,800 B1 | 11/2002 | Fraser et al. | |
| 6,514,256 B2 | 2/2003 | Zucherman et al. | |
| 6,530,926 B1 | 3/2003 | Davison | |
| 6,569,169 B2 * | 5/2003 | De La Barrera et al. | 606/102 |
| 6,599,294 B2 * | 7/2003 | Fuss et al. | 606/99 |
| 6,626,944 B1 | 9/2003 | Taylor | |
| 2001/0020170 A1 | 9/2001 | Zucherman et al. | |
| 2001/0021853 A1 | 9/2001 | Heckele et al. | |
| 2002/0045904 A1 | 4/2002 | Fuss et al. | |
| 2002/0072752 A1 | 6/2002 | Zucherman et al. | |
| 2002/0099377 A1 | 7/2002 | Zucherman et al. | |
| 2002/0116009 A1 | 8/2002 | Fraser et al. | |
| 2003/0083747 A1 | 5/2003 | Winterbottom et al. | |
| 2003/0105466 A1 | 6/2003 | Ralph et al. | |
| 2004/0153088 A1 | 8/2004 | Ralph et al. | |
| 2004/0162617 A1 | 8/2004 | Zucherman et al. | |

FOREIGN PATENT DOCUMENTS

| | | |
|---|---|---|
| EP | 1 323 396 A | 7/2003 |
| WO | WO 03/008016 | 1/2003 |
| WO | WO 03/037228 A | 5/2003 |

* cited by examiner

Primary Examiner—Pedro Philogene
(74) Attorney, Agent, or Firm—Krieg DeVault LLP

(57) ABSTRACT

An implant inserter is releasably engageable to an implant to facilitate placement of the implant in a minimally invasive approach to space between adjacent spinous processes. The implant inserter can engage the implant in a first configuration for insertion and thereafter remotely release the implant for engagement with the spinous processes in the patient.

49 Claims, 15 Drawing Sheets

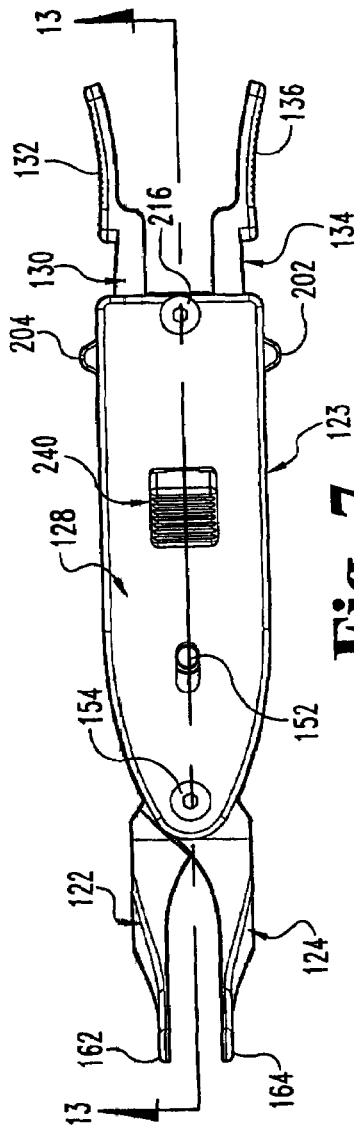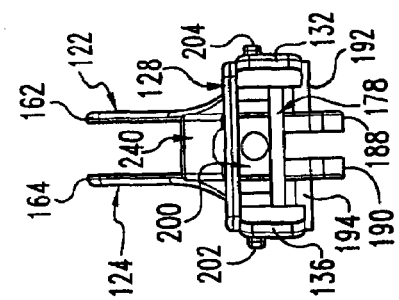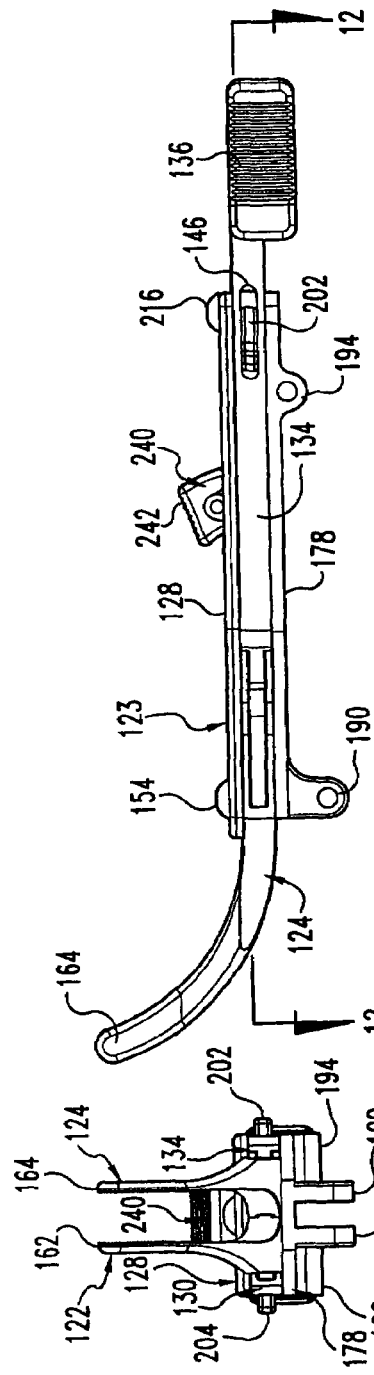

DEVICES AND METHODS FOR INSERTING SPINAL IMPLANTS

BACKGROUND

The present invention relates to surgical instrumentation and techniques, and, more particularly, to surgical instruments and techniques for inserting implants.

Surgery for a patient can be painful and traumatic, particularly in the affected area of the patient's body. For example, the dissection and retraction required to access the surgical site in the patient can cause trauma to the dissected and retracted tissue as well as to the surrounding tissue. The tissue must heal properly for satisfactory patient recovery, and scar tissue can even result when the affected tissue heals.

Tissue dissection and retraction can be required to insert an implant in a patient to a surgical site. Some procedures involve mounting the implant on an instrument that holds the implant as it is inserted to the surgical site. To accommodate implant insertion, sufficient muscle and vasculature and other tissue must be dissected and retracted to allow passage of the implant therethrough.

In certain procedures, multiple incisions and/or large openings in the patient are required to place the implant at the desired anatomical location. In other procedures, the implant must be accessed after implantation to provide the desired fit or positioning relative to the patient. Still other procedures require the implant to be modified for insertion.

There remains a need for instruments and methods that can be employed for implant insertion that minimize or facilitate the minimization of tissue dissection and retraction, exposure of the patient's body to the surgical procedure, and handling or manipulation of an implant during and after insertion. The present invention is directed to meeting these needs, among others.

SUMMARY

An implant inserter is releasably engageable to an implant to facilitate placement of the implant in a minimally invasive approach to space between adjacent spinous processes. The implant inserter can engage the implant in a first configuration for insertion and thereafter remotely release the implant for engagement with the spinous processes in the patient. The implant inserter also has application in invasive surgical procedures and also with implants for other bony structures.

According to one aspect, a surgical instrument for inserting an implant includes a handle assembly at a proximal end of the instrument and an actuator assembly extending along a longitudinal axis that is operably coupled with said handle assembly. An implant engaging portion is provided at a distal end of the instrument. The implant engaging portion includes a holder positionable in contact with the implant and a clamp assembly coupled with the actuator assembly. The clamp assembly includes a pair of distal arm portions adjacent the holder that are movable toward one another to engage the implant therebetween. The distal arm portions are movable proximally relative to the holder with the actuator assembly upon manipulation of the handle assembly to release the implant from between the distal arm portions while the holder maintains contact with the implant.

According to another aspect, a surgical instrument for inserting an implant includes a handle assembly and a clamp assembly extending from the handle assembly along a longitudinal axis. The clamp assembly includes a pair of distal arm portions to engage the implant therebetween. An implant engaging portion is provided at a distal end of the instrument. The implant engaging portion includes a holder positionable in contact with the implant and the pair of distal arm portions are adjacent the holder. The distal arm portions are movable relative to one another to engage the implant therebetween with the holder in contact with the implant. The holder and the distal arm portions are each offset to a first side of the longitudinal axis.

According to a further aspect, a surgical instrument for inserting an implant includes a handle assembly at a proximal end of the instrument and an actuator assembly extending along a longitudinal axis. An implant engaging portion is provided at a distal end of the instrument. The implant engaging portion includes a holder positionable in contact with the implant and a clamp assembly. The clamp assembly includes a pair of distal arm portions adjacent the holder that are movable toward one another to engage the implant therebetween. The actuator assembly is operably coupled between the handle assembly and the clamp assembly. The actuator assembly is manipulatable with the handle assembly to translate the distal arm portions away from the holder and toward the longitudinal axis.

In another aspect, a surgical instrument for inserting an implant includes a handle assembly at a proximal end of the instrument. An implant engaging portion is provided at a distal end of the instrument. The instrument extends along a longitudinal axis between its proximal and distal ends. The implant engaging portion including a holder positionable in contact with the implant and a pair of distal arm portions adjacent the holder. The distal arm portions are movable toward one another to engage the implant therebetween. The instrument includes means for coupling the handle assembly with the implant engaging portion that is operable with the handle assembly to translate the pair of distal arm portions proximally and transversely to the longitudinal axis away from the holder.

In a further aspect, a surgical method for inserting an implant between adjacent spinous processes, comprises: forming an opening laterally offset from a spinal midline and adjacent the adjacent spinous processes; holding an implant in a reduced size configuration; inserting the implant through the opening and between the spinous processes while maintaining the reduced size configuration through the opening; and releasing the inserted implant to engage the spinous processes on each side of the spinal midline with the implant.

In another aspect, a method for holding a spinal implant for insertion into space between adjacent bony portions of the spinal column comprises: positioning the spinal implant in a holder; compressing at least a portion of the spinal implant extending from the holder; positioning the compressed portion of the spinal implant through a space between the adjacent bony portions; and releasing the compressed portion of the spinal implant to engage the implant to the adjacent bony portions while maintaining engagement of the spinal implant with the holder.

These and other aspects are discussed further below.

BRIEF DESCRIPTION OF THE DRAWINGS

FIG. 7 is a top view of a clamp assembly comprising a portion of the implant inserter of FIG. 1.

FIG. 8 is a side elevational view of the clamp assembly of FIG. 7.

FIG. 9 is a right end view of the clamp assembly of FIG. 7.

FIG. 10 is a left end view of the clamp assembly of FIG. 7.

DETAILED DESCRIPTION

Figure 1:
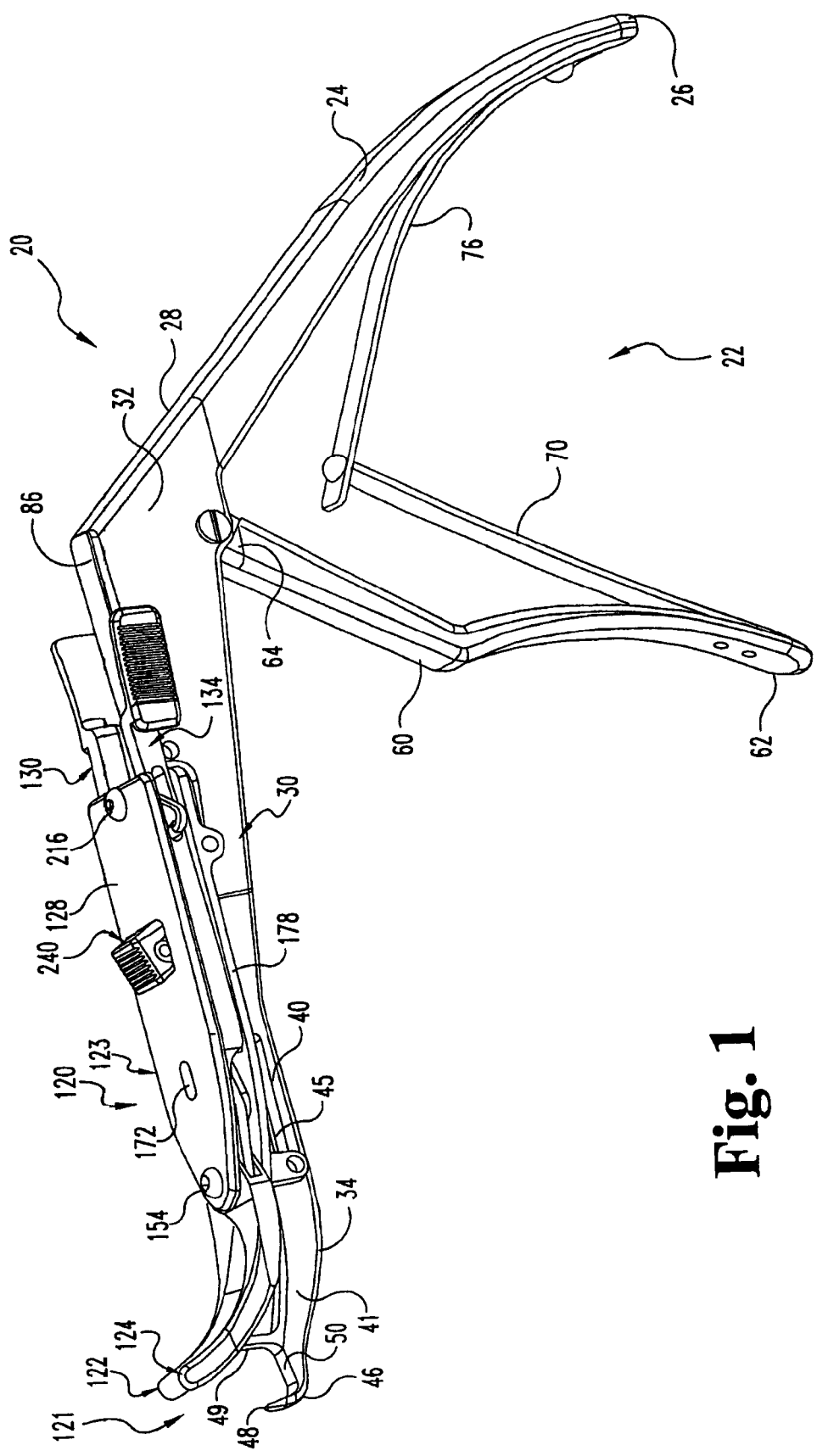
FIG. 1 is a perspective view of an implant inserter.
Figure 2:
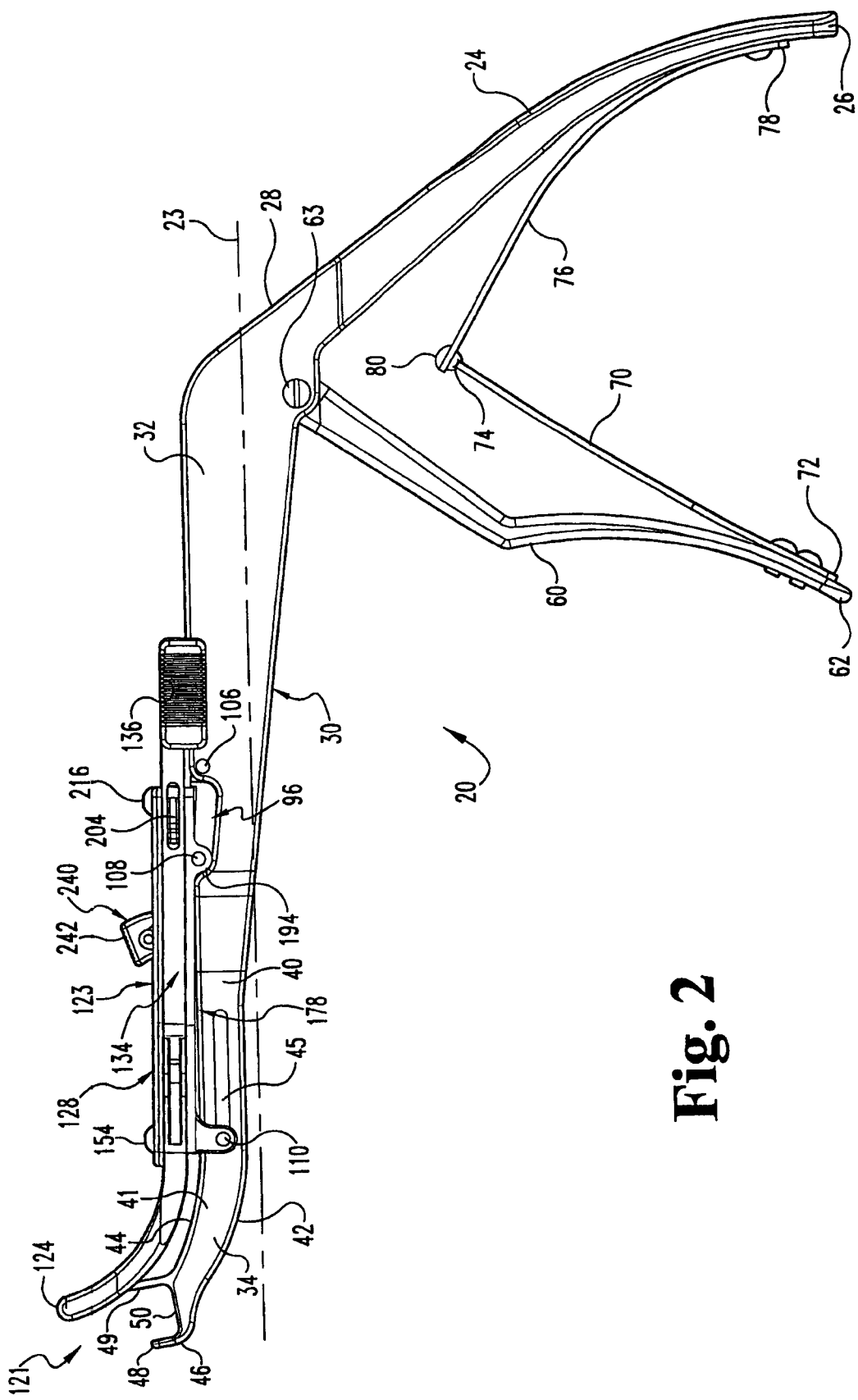
FIG. 2 is a side elevational view of the implant inserter of FIG. 1.
Figure 3:
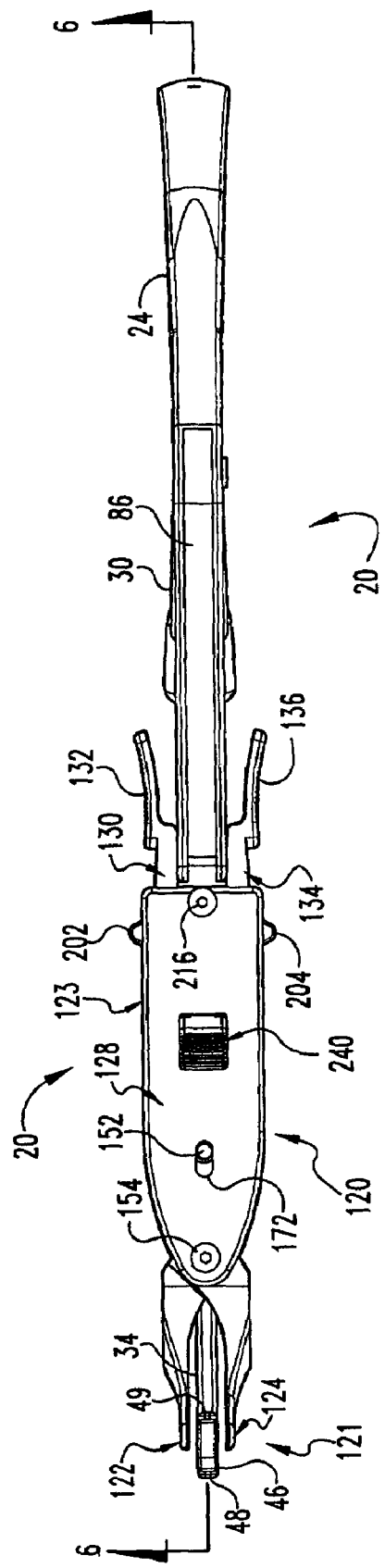
FIG. 3 is a top view of the implant inserter of FIG. 2.
Figure 4:
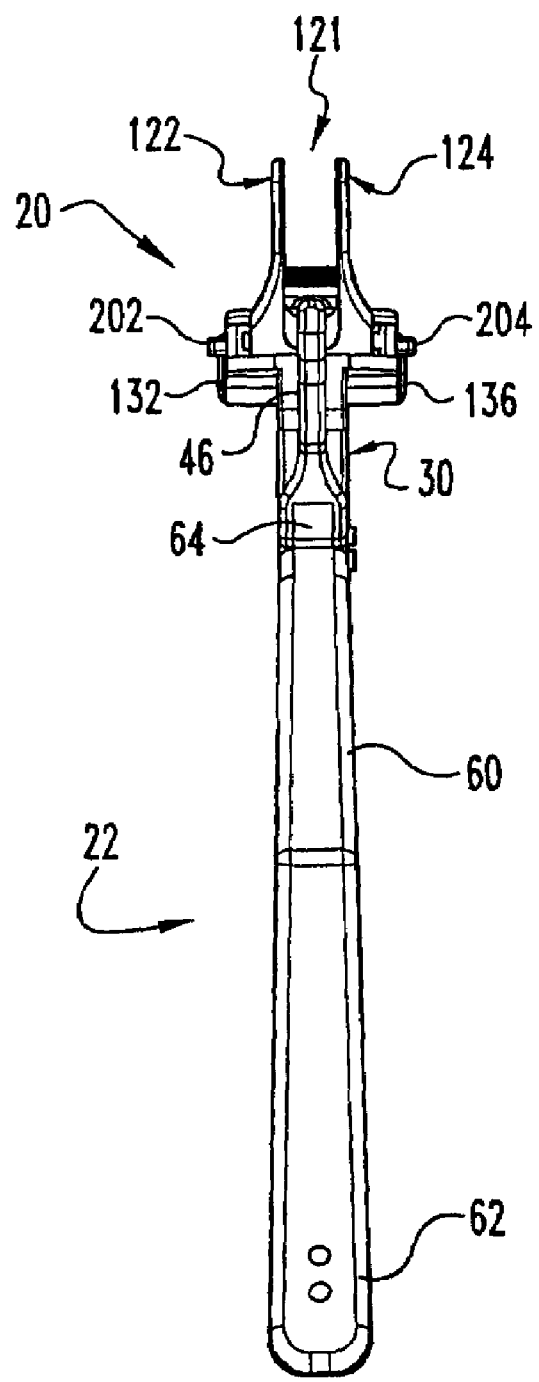
FIG. 4 is a left end view of the implant inserter of FIG. 2.
Figure 5:
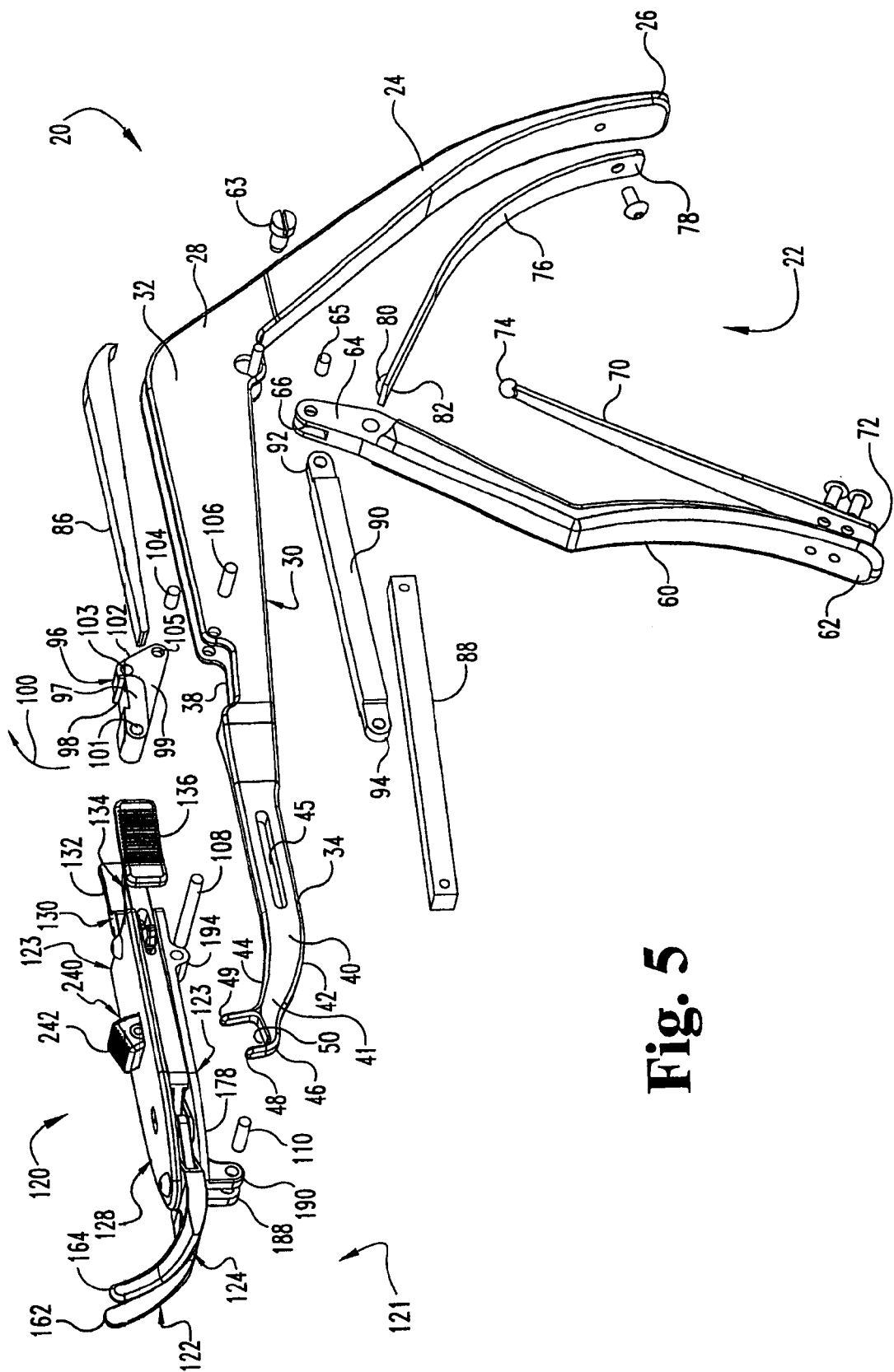
FIG. 5 is an exploded view of the implant inserter of FIG. 1.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

In FIG. 1, there is shown an implant inserter 20 for inserting an implant between adjacent bony portions of a spinal column segment. While implant inserter 20 is particularly useful in a minimally invasive approach to position an implant between adjacent spinous processes, implant inserter 20 also has application in invasive surgical procedures, and for inserting implants between other bony structures. Inserter 20 can be positioned through a minimally invasive surgical portal to position and engage the implant at the operative site, such portals may be formed by one or more guide sleeves, micro-incisions, or retractor blades, for example. Insertion of the implant can be monitored by any one or combination of naked eye, endoscopic, microscopic, loupes, fluoroscopic, X-ray, CT scan, and radiographic viewing techniques.

Implant inserter 20 includes a distal implant engaging portion 121 remotely operable with an actuator assembly 125 (FIG. 6) by manipulating a proximal handle assembly 22. Engaging portion 121 includes a first configuration for holding an implant for insertion between adjacent spinous processes, and after implant insertion is movable with handle assembly 22 to a second configuration to at least partially release the implant and engage the implant to the adjacent spinous processes. In the second configuration, engaging portion 121 assumes a low profile relative to a longitudinal axis of the instrument to facilitate withdrawal of engaging portion 121 from the surgical space. In addition, the implant can be held in an insertion configuration with engaging portion 121 in its first configuration, and the implant is released for implantation at the surgical site when engaging portion 121 is in its second configuration. In one embodiment, the insertion configuration of the implant includes placing the implant in a reduced size with engaging portion 121 to facilitate insertion through a minimally invasive access portal and/or between adjacent spinous processes. In the implanted position engaging portion 121 is released from the implant and the implant expands or otherwise assumes a configuration that differs from the insertion configuration to engage the adjacent spinous processes.

Implant inserter 20 includes engaging portion 121 which includes a holder 46 at a distal end of an implant holder arm 30, and first and second clamping members 122, 124 extending distally from a clamp assembly 120. In the illustrated embodiment, holder arm 30 is fixed relative to handle assembly 22, and clamp assembly 120 is movable along longitudinal axis 23 of implant inserter 20 with actuator assembly 125 operably coupled to handle assembly 22. Clamp assembly 120 includes first and second lever arms 130, 134 coupled to clamping members 122, 124. Lever arms 130, 134 are operable to move clamping members 122, 124 toward and away from on another and transversely to longitudinal axis 23 to grip and release an implant positioned therebetween.

Clamp assembly 120 is movable relative to holder arm 30 to facilitate release of an implant engaged between clamping members 122, 124 while holder 46 maintains the implant in the implanted position. Clamp assembly 120 is movable with actuator assembly 125 by manipulating handle assembly 22 to move clamping members 122, 124 simultaneously proximally and toward longitudinal axis 23 to provide engaging portion 121 with a reduced profile along longitudinal axis 23. The reduced profile of engaging portion 121 includes positioning clamping members 122, 124 in substantial alignment with holder arm 30 to facilitate withdrawal of engaging portion 121 from the operative site where the implant is positioned. In one embodiment, clamping members 122, 124 are simultaneously moved proximally and toward longitudinal axis 23 by pivoting and proximally translating the distal end of clamp assembly 120 relative to holder arm 30 through elevation of a proximal end of clamp assembly 120 away from longitudinal axis 23 with actuator assembly 125.

Handle assembly 22 includes a second handle member 60 pivotally coupled to a first handle member 24. First handle member 24 includes an outer end 26 and an opposite junction end 28. Second handle member 60 includes an outer end 62 and an opposite pivot end 64. Pivot end 64 is pivotally coupled to first handle member 24 adjacent its junction end 28.

Figure 16:
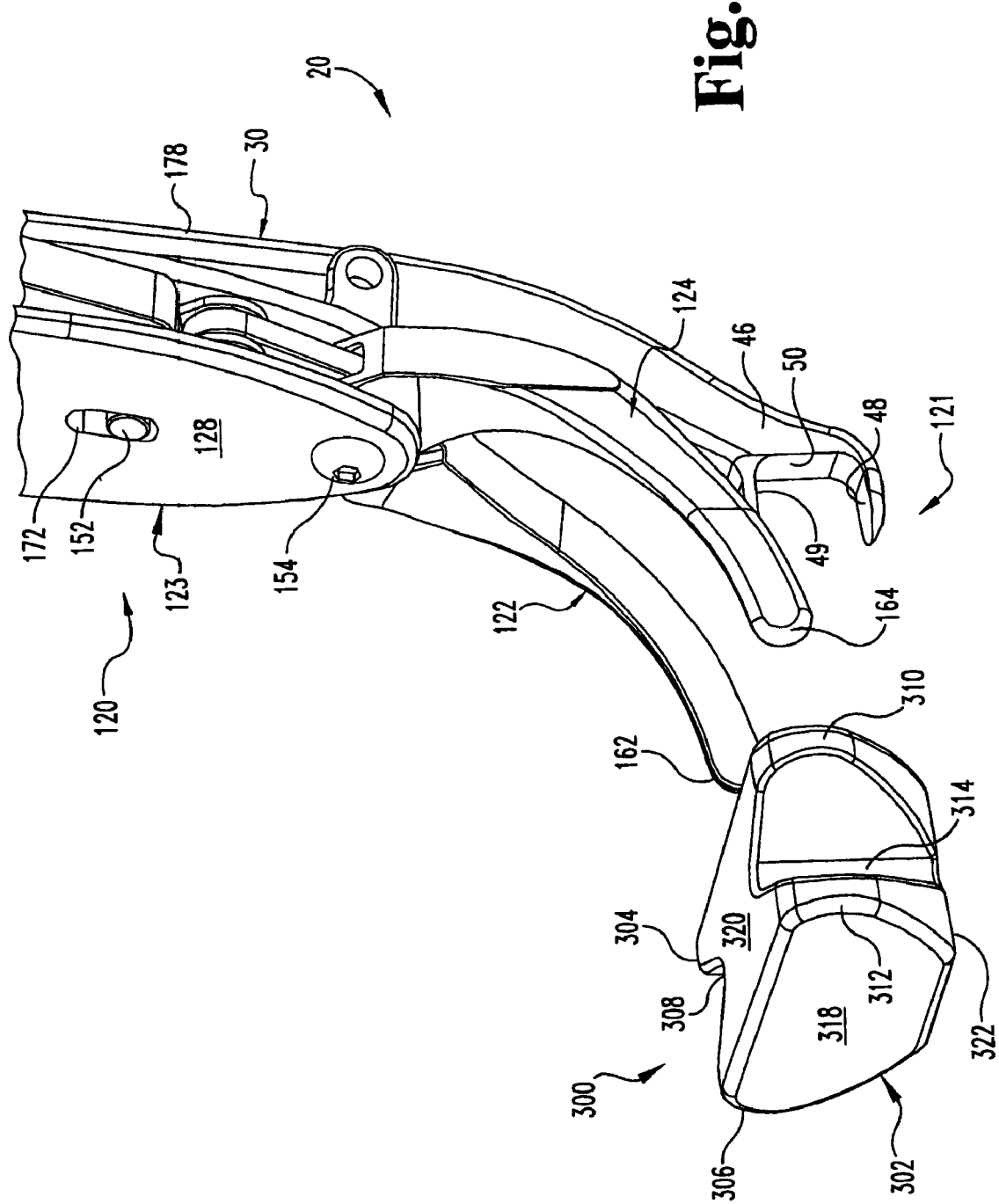
FIG. 16 is a perspective view of a distal portion of the implant inserter of FIG. 1 in a release position adjacent the implant of FIG. 14.

Outer ends 26, 62 of handle member 24, 60 can be biased away from one another with a spring assembly comprising a first spring arm 70 and a second spring arm 76. First spring arm 70 includes an outer end 72 coupled to outer end 62 of second handle member 60. Second spring arm 76 includes an outer end 78 coupled to outer end 26 of first handle member 24. First spring arm 70 includes a ball member 74 opposite outer end 72 that is received in a detent 82 of detent member 80 at the end of second spring arm 76 opposite first end 78. Spring arms 70, 76 bias handle assembly 22 so that clamping members 122, 124 of clamp assembly 120 are biased distally toward holder 46 and located relative thereto to clamp an implant positioned in holder 46, as shown in FIG. 16.

Holder arm 30 extends transversely to first handle member 26 and is integrally formed therewith at junction end 28. Holder arm 30 includes a proximal arm portion 32 and a distal arm portion 34 extending along longitudinal axis 23. Proximal arm portion 32 includes a receptacle 36 (FIG. 6) therein, and a crank member recess 38 along an upper side thereof. Holder arm 30 can be tapered along proximal arm portion 32 and distal arm portion 34.

Distal arm portion 34 of holder arm 30 further includes a linear portion 40 defining a laterally opening elongated slot 45 therethrough. Extending distally from linear portion 40 is a curved portion 41 having an upper curved surface 44 and an opposite lower curved surface 42 therealong. Curved portion 41 is curved such that its distal end extends away from longitudinal axis 23 in a first direction that is opposite the direction in which handle assembly 22 extends from longitudinal axis 23. Holder 46 is located at the distal end of curved portion 41 and is offset to the first side of longitudinal axis 23.

Holder 46 includes a first extension 48, a second extension 49, and a cradle surface 50 therebetween. Holder extensions 48, 49 extend away from longitudinal axis 23, and provide an opening therebetween that opens toward the first side of longitudinal axis 23. As discussed further below, an implant can be positioned between holder extensions 48, 49 and rest on cradle surface 50. Holder extensions 48, 49 extend along sidewalls of the implant to provide frictional engagement therewith and to prevent the implant from easily falling out of holder 46. Holder 46 can further be employed to re-position the implant at the operative site when clamping members 122, 124 are released from the implant. With the implant engaged to the adjacent bony structure, holder extensions 48, 49 can slide along the implant as inserter instrument 20 is withdrawn from the operative site to release the implant from between holder extensions 48, 49.

Holder extensions 48, 49 are immovable extensions that form a C-shaped cradle surface 50 therebetween in the illustrated embodiment. Other embodiments contemplate other configurations for holder 46, including differing shaped cradle surfaces and one or more extensions 48, 49 that are movable relative to one another. In addition, it is contemplated that holder 46 could be provided with a single extension, or with three or more extensions.

Second handle member 60 is further pivotally coupled to a link member 90 adjacent its pivot end 64. Link member 90 includes a proximal end 92 and an opposite distal end 94. Proximal end 92 of link member 90 is pivotally coupled to second handle member 60 with a first link pin 65. Link member 90 is received within and movable within receptacle 36 in response to movement of second handle member 60 relative to first handle member 24. An upper cover plate 86 extends along an upper side of proximal portion 32 of holder arm 30, and a lower cover plate 88 extends along a lower side of proximal portion 32. Cover plates 86, 88 can be integral or removable with proximal portion 32, and protect link member 90 and the components connected thereto in receptacle 36.

Crank member 96 includes a triangular shaped body with a rotational center 103 pivotally coupled to holder arm 30 with first crank pin 106. Crank member 96 is pivotally coupled to holder arm 30 and rotates about first crank pin 106 in response to movement of link member 90 through manipulation of handle assembly 22. Crank member 96 also includes a lower apex 103 pivotally coupled to distal end 94 of link member 90 with second crank pin 104. Crank member 96 further includes a distal, upper apex 101 that is pivotally coupled to the proximal end of clamp assembly 120 with third crank pin 108. The distal end of clamp assembly 120 is pivotally and translatably secured in slot 45 of holder arm 30 with holder arm pin 110.

Figure 20:
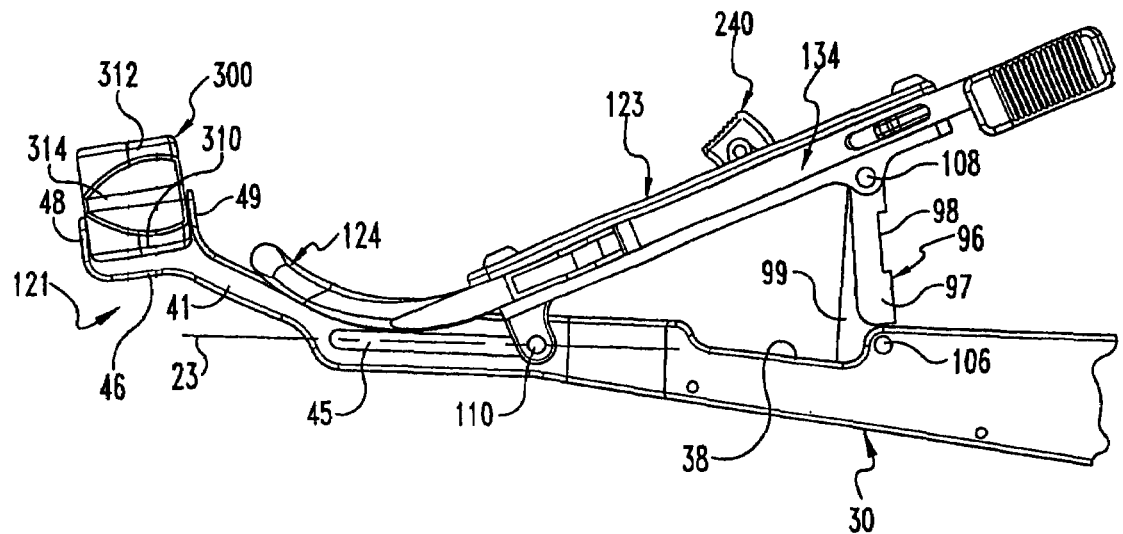
FIG. 20 is a side elevational view of a distal portion of the implant inserter of FIG. 1 in a low profile configuration and released from the implant of FIG. 14.

As crank member 30 is rotated about its rotational center 103 in the direction of arrow 100 with link member 90, lower apex 103 translates along an arc distally and toward longitudinal axis 23, and distal upper apex 101 translates along an arc proximally and away from longitudinal axis 23. Distal upper apex 101 of crank member 96 lifts the proximal end of clamp assembly 120 away from longitudinal axis 23 and further displaces the proximal end of clamp assembly 120 proximally. The distal end of clamp assembly 120 pivots in and moves proximally along longitudinal axis 23 in slot 45 as the proximal end of clamp assembly 120 is moved with crank member 96. This movement of clamp assembly 120 is followed by clamping members 122, 124, thus moving clamping members 122, 124 toward longitudinal axis 23 and along curved portion 41 of holder arm 30, as shown in FIG. 20. In this position, clamping members 122, 124 move away from holder 46 and engaging portion 121 includes a low profile along longitudinal axis 23, facilitating withdrawal of engaging portion 121 from the surgical site.

Figure 6:
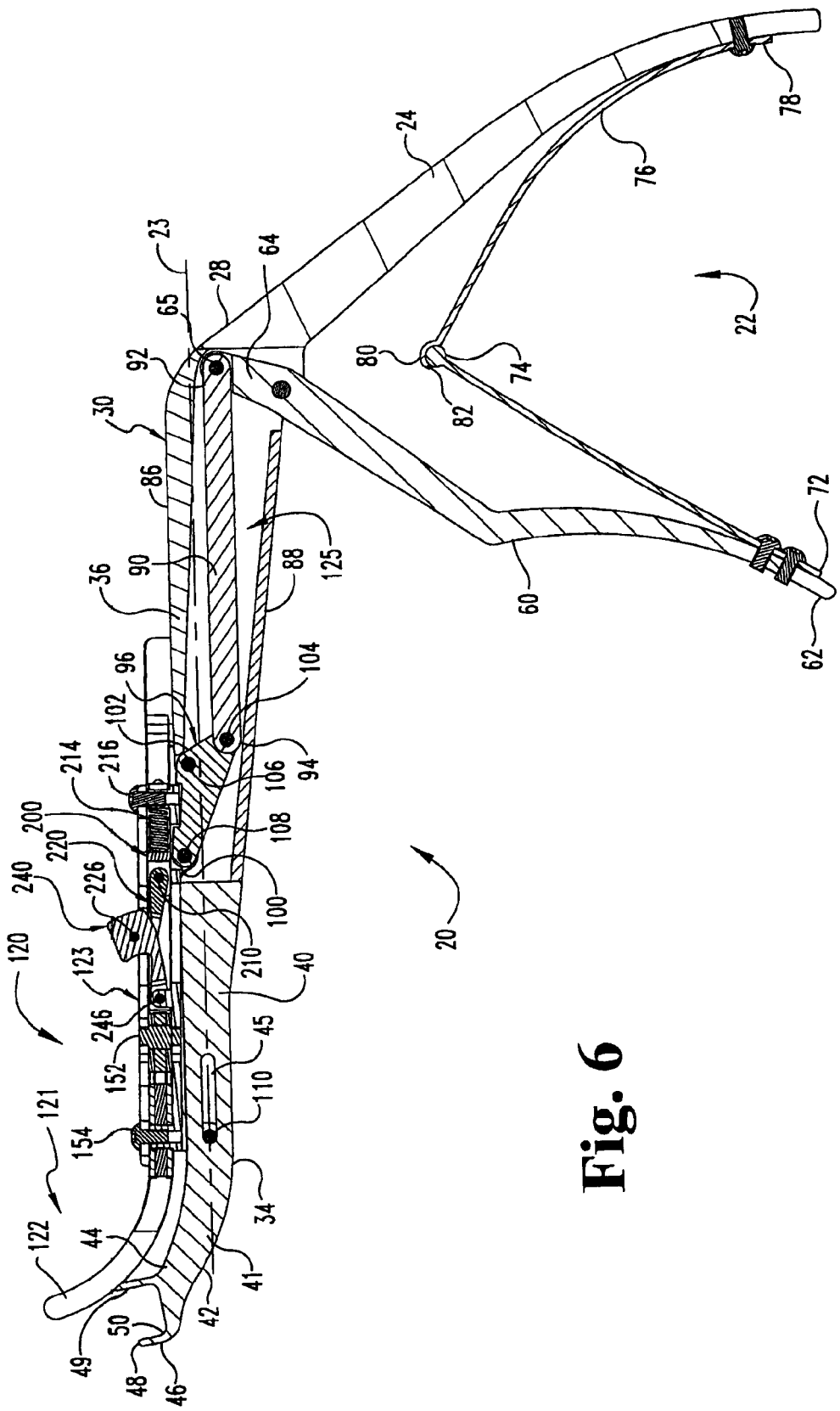
FIG. 6 is a section view along line 6-6 of FIG. 3.
Figure 11:
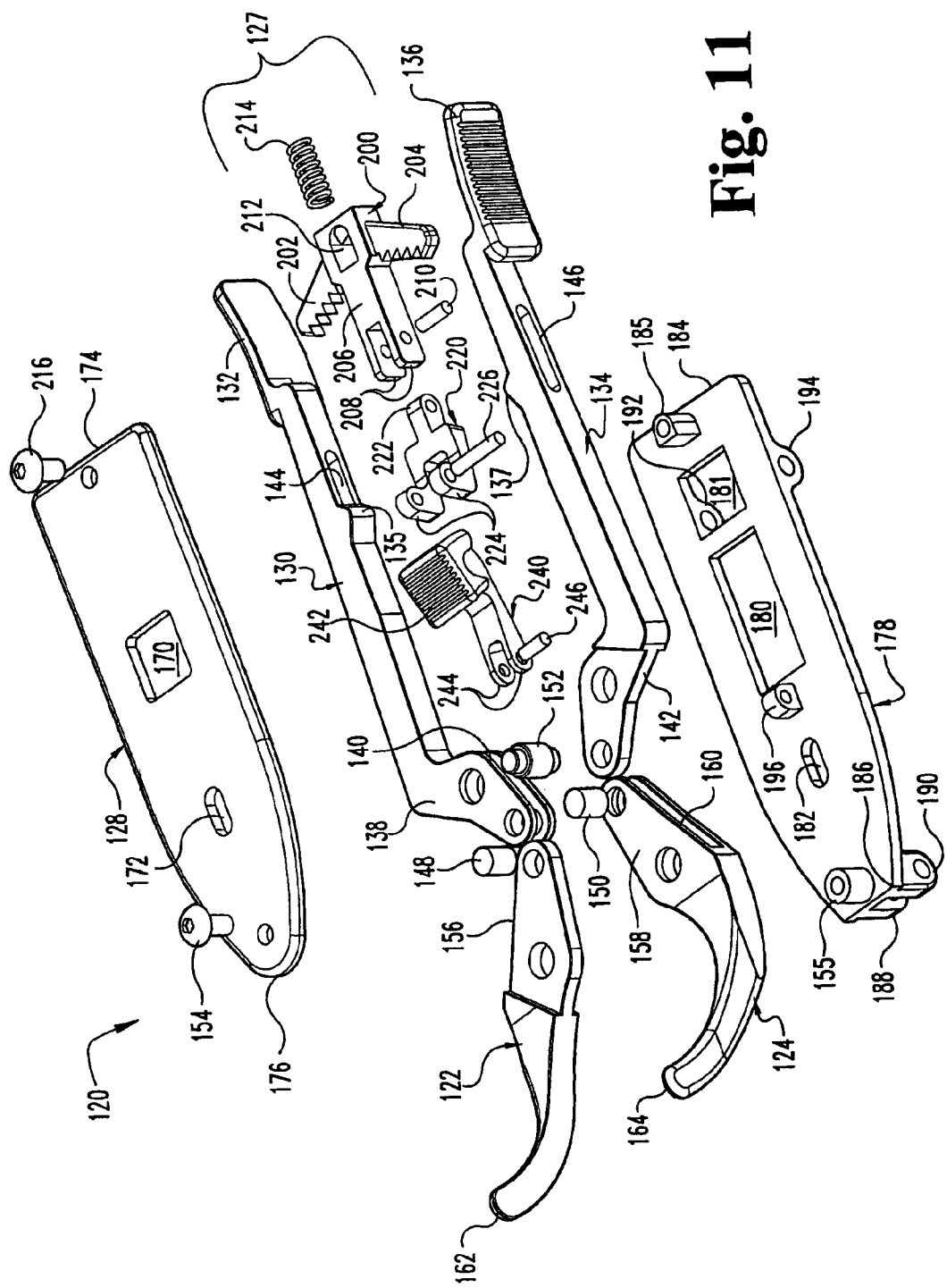
FIG. 11 is an exploded perspective view of the clamp assembly of FIG. 7.
Figure 12:
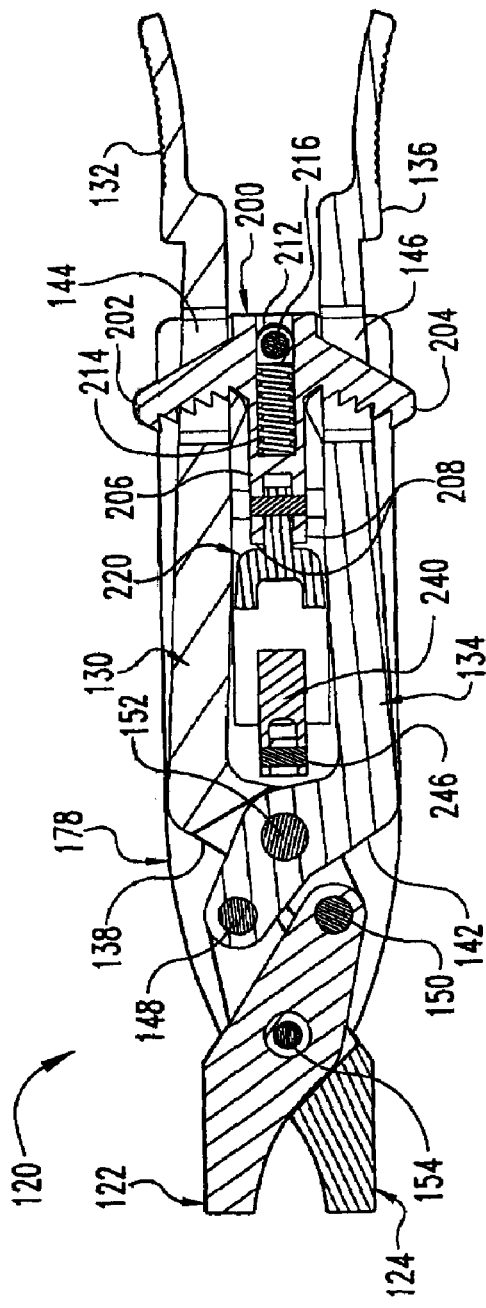
FIG. 12 is a section view through line 12-12 of FIG. 8.
Figure 13:
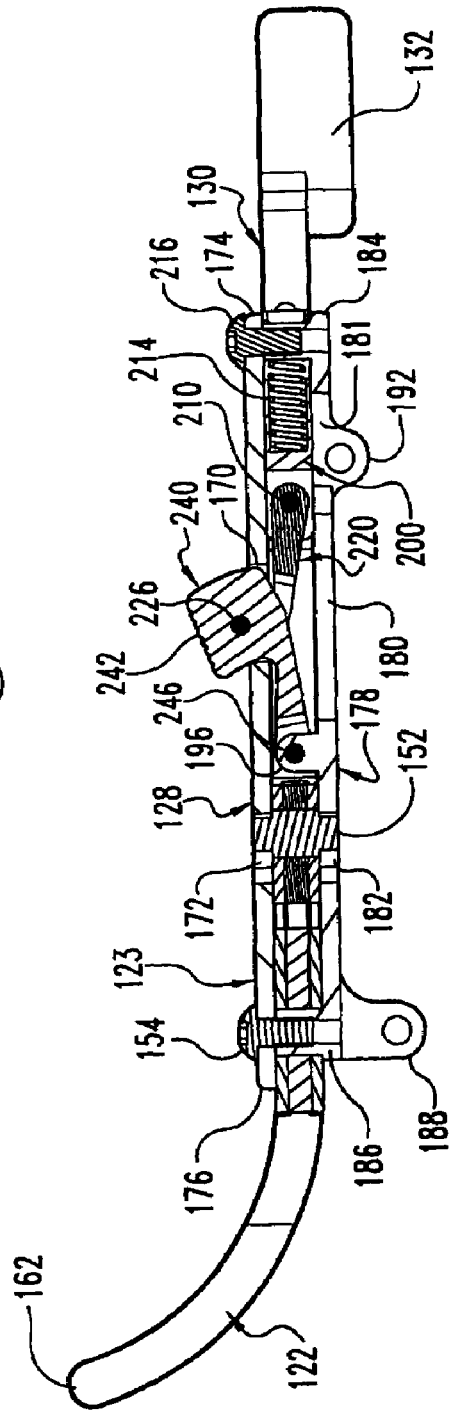
FIG. 13 is a section view through line 13-13 of FIG. 7.

Crank member 96 further includes a lower body portion 99 and an upper body portion 97 protruding laterally from lower body portion 99. Upper body portion 97 fits within crank recess 38 of holder arm 30 when clamp assembly 120 is in its undeployed position, as shown in FIG. 6, while lower body portion 99 extends into receptacle 36. Upper body portion 97 supports crank member 36 on holder arm 30 in recess 38 to maintain a desired relative orientation between crank member 96 and clamp assembly 120 in the undeployed position. As clamp assembly 120 is deployed with handle assembly 22, the proximal end of upper body portion 97 rotates about the proximal end of recess 38 as the remainder of the body of crank member 96 is lifted from recess 38.

Referring to FIGS. 7-13, further details of clamp assembly 120 will be discussed. Clamp assembly 120 include includes a housing 123 slidably and pivotally coupled to holder arm 30, and also pivotally coupled to second handle 60 actuator assembly 125. Housing 123 houses a lever arm locking assembly 127 and also lever arms 130, 134 between upper and lower cover plates 128, 178. Clamping members 122, 124 project distally from housing 123 for engagement with an implant therebetween. Clamping member fastener 154 and lock spring fastener 216 couple upper and lower plates 128, 178 to one another.

In the illustrated embodiment, upper plate 128 extends between a proximal end 174 and a distal end 176. Upper plate 128 is bullet shaped with a distal end taper to facilitate placement in minimally invasive surgical procedures. Upper plate 128 includes a lock button window 170 and an indicator window 172 extending therethrough. Lock button 240 projects through lock button window 170 for access by the surgeon to manipulate the lever arm locking assembly 127, as discussed further below.

Lower plate 178 includes a body and extends between a proximal end 184 and a distal end 186. Lower plate 178 includes a locking assembly window 180 which facilitates movement of the lever arm locking assembly 127 in housing 123 to release lever arms 130,134. Cover plate 178 further includes a proximal window 181 which receives crank member 96 as it is pivoted with link member 90 to deploy and undeploy clamp assembly 120 as discussed above. Lower plate 178 further includes a distal plate window 182 which receives a lower portion of indicator pin 152. Indicator pin 152 pivotally couples lever arms 130, 134 to one another and also to upper and lower plates 128, 178. Lower plate 178 includes distal ears 188, 190, which are slidable or translatable along and pivotally coupled with slot 45 by holder arm pin 110. Lower plate 178 further includes first and second proximal ears 192, 194 which receive second crank pivot pin 108. Second crank pivot pin 108 pivotally couples lower plate 178, and thus clamp assembly 120, to crank member 96.

First clamping member 122 includes a distal arm portion 162 and a proximal end flange 156 angled relative thereto and including a proximal hole and a distal hole. Similarly, second clamping member 124 includes a distal arm portion 164 and a proximal end flange 158 angled relative thereto including a proximal hole and a distal hole. Proximal end flange 158 includes a clamping member slot 160 to receive proximal end flange 156 of first clamping member 122 therethrough with distal arm portions 162, 164 extending parallel to one another along longitudinal axis 23, and with the distal holes aligned with one another. Clamping members 122, 124 are pivotally coupled to one another and to housing 123 with a clamping member fastener 154 and post 155 extending through the aligned distal holes in flanges 156, 158.

Clamp assembly 120 further includes first and second lever arms 130, 134. First lever arm 130 includes a proximal end 132 and a distal end flange 138 angled relative thereto. Distal end flange 138 defines a slot 140 and includes a proximal hole and a distal hole. Second lever arm 134 includes a proximal end 136 and a distal end flange 142. Distal end flange 142 includes a proximal hole and a distal hole, and is positionable through slot 140 of first lever arm 130 with the proximal holes aligned with one another. Lever arm 130 is pivotally coupled to lever arm 134 with an indicator pin 152 extending through the aligned proximal holes.

In order to move first and second clamping members 122, 124 relative to one another, the proximal hole in proximal end flange 158 of second clamping member 124 is engaged with the distal hole in distal end flange 142 of second lever arm 134 with first clamping arm pin 148. In a similar manner, the distal hole of distal end flange 138 of first lever arm 130 is coupled to the proximal hole in the proximal end flange 156 of first clamping arm 122 with second lever pin 150.

Lever arms 130, 134 can be pivoted away from longitudinal axis 23 about indicator pin 152 to pivot distal arm portions 162, 164 of clamping members 122, 124 about post 155 and away from one another to release an implant positioned therebetween. Lever arms 130, 134 are pivoted toward longitudinal axis 23 to move distal arm portions 162, 164 of clamping members 122, 124 toward one another to engage an implant therebetween. It is further contemplated that locking mechanism 127 can be provided to secure lever arms 130,134 to housing 123 and thus preventing clamping members 122, 124 from moving relative to one another.

Distal arm portions 162, 164 of first and second clamping members 122, 124 each include a curved profile such that the distal ends of clamping members 122, 124 are transversely oriented to longitudinal axis 23 and directed away from longitudinal axis 23. The curved profile of distal arm portions 162, 164 mimics that of curved portion 41 of holder arm 30. The curved profile of engaging portion 121 facilitates insertion of an implant held by engaging portion 121 along an insertion path that is transverse to longitudinal axis 23. For example, a minimally invasive approach to position an implant between adjacent spinous processes can include approaching the spinous process from a posterior entrance location that is laterally offset from the spinal mid-line. Accordingly, the implant must be advanced anteriorly into the entrance location and also medially to a location between the adjacent spinous processes. The curved profile of engaging portion 121 facilitates the positioning of an implant along such an insertion path while minimizing the amount of tissue excision and retraction required.

Clamp assembly 120 also includes lever arm locking assembly 127 which comprises a lock member 200, a coupling member 220, and a lock button 240. Lock member 200 includes a first locking arm 202 and a second locking arm 204 extending from a lock body 206. A pair of lock ears 208 extend distally from lock body 206. Lock member 200 is positioned between first and second lever arms 130, 134 with first locking arm 202 extending through a first lever arm window 144, and second locking arm 204 extending through a second lever arm window 146. Locking arms 202, 204 each include a distally oriented ratchet surface, and are angled so that the outer end of each arm 202, 204 is offset distally relative to the medial end of each arm 202, 204.

Lever arm 130 includes a medially oriented protrusion 135 and window 144 extending proximally therefrom. Similarly, lever arm 134 includes a medially oriented protrusion 137, and window 146 extending proximally therefrom. Locking arm 202 extends through window 144, and locking arm 204 extends through window 146. Protrusions 135, 137 engage the adjacent ratchet surface of the locking arm 202, 204 positioned through the respective window 144, 146. The angled locking arms 202, 204 and their respective ratchet surfaces maintain engagement with lever arms 130, 134 to maintain the relative positioning between clamping members 122, 124.

Locking arms 202, 204 are normally biased distally so that the ratchet surface is normally engaged to the adjacent protrusion 135, 137. Lock body 206 includes a receptacle 212 opening proximally which houses a lock spring 214. Lock spring 214 is maintained within receptacle 212 with a lock spring fastener 216 and post 185 extending at the proximal end opening of receptacle 212. Lock spring 214 is compressed between post 185 of lower plate 178 and a distal wall in receptacle 212 to bias locking arms 202, 204 distally and maintain locking arms 202, 204 in engagement with the respective protrusion 135, 137.

In order to release locking arms 202, 204 from their engagement with protrusions 135, 137, and thus allow lever arms 132, 134 to be pivoted relative to one another, a lock release button 240 is provided. Lock release button 240 is pressed to move lock member 200 proximally against the bias of lock spring 214, thus moving locking arms 202, 204 proximally and out of engagement with protrusions 135, 137.

A coupling member 220 extends between and pivotally couples lock release button 240 to lock member 200. Coupling member 220 includes proximal ear 222 pivotally coupled to lock ears 208 of lock member 200 with a lock pin 210. Coupling member 220 further includes distal coupling member ears 224. Coupling member ears 224 are pivotally coupled to lock button 240 with a first button pin 226 extending through ears 224 and lock release button 240.

Lock release button 240 includes an upper serrated or roughened surface 242 for facilitating engagement by the fingers of a surgeon to move lock release button 240 downwardly. Lock release button 240 further includes button ears 244 extending distally therefrom. A second button pin 246 extends through button ears 244 to pivotally couple lock release button 240 to housing 123. For example, in the illustrated embodiment lock release button 240 is pivotally coupled at its distal end to a protrusion 196 extending from a bottom plate 178 of housing 123. Coupling member 220 biases upper surface 242 through window 170 of upper plate 128 to facilitate access by the surgeon. The downwardly applied force to lock release button 240 is translated with coupling member 220 into a proximally directed translation force to lock member 200, compressing lock spring 214 and disengaging locking arms 202, 204 from lever arms 130, 134, respectively. When disengaged, the lever arms 130, 134 can be pivoted away from longitudinal axis 23, thus moving clamping members 122, 124 away from one another. When lock release button 240 is released, and lever arms 130, 134 are moved sufficiently toward longitudinal axis 23, lock spring 214 biases locking arms 202, 204 into engagement with lever arms 130, 134. Coupling member 220 translates the axially and distally directed force applied by lock spring 214 into a pivotal force to bias lock release button 240 through lock button window 170 of upper plate 128.

Indicator pin 152 extends at least partially into indicator window 172 of upper plate 128, and its positioning relative to window 172 provides an indication of the positioning of clamping members 122, 124 relative to one another. Clamping members 122, 124 are pivotally coupled and fixed proximally and distally relative to housing 123 with clamping arm fastener 154. The clamping action between clamping members 122, 124 is provided by pivotally moving lever arms 130, 134 toward longitudinal axis 23 and between cover plates 128, 178. In FIG. 7 indicator pin 152 is proximally located in indicator window 172, indicating that clamping members 122, 124 are positioned adjacent one another. To separate clamping members 122, 124, lever arms 130, 134 are pivoted away from longitudinal axis 23 and out from the space between cover plates 128, 178, therefore displacing lever arms 130, 134 distally in upper plate window 172 (and also in distal window 182 of lower plate 178.) Contact between the distal ends of windows 172, 182 and indicator pin 152 limits the distal movement of indicator pin 152 and thus the separation of clamping members 122, 124 with lever arms 130, 134.

Figure 14:
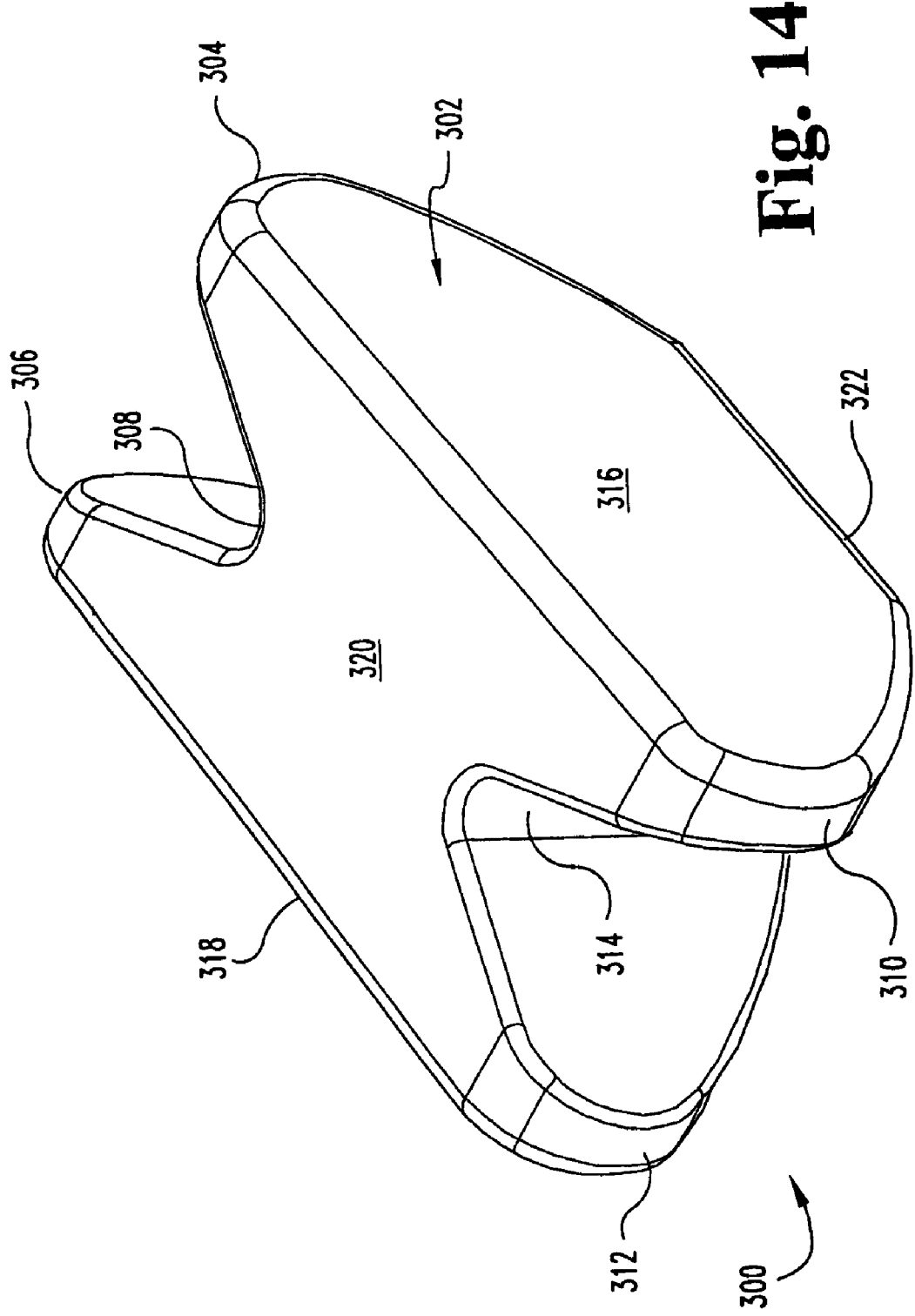
FIG. 14 is a perspective view of one embodiment of an implant insertable with the implant inserter of FIG. 1.

In FIG. 14 there is shown an implant 300 particularly suited for placement between adjacent bony portions of the spinal column, such as adjacent spinous processes. Implant 300 can also be positioned between other bony structures, such as between divided lamina, adjacent vertebral endplates, other bony structures associated with the spinal column. Implant 300 includes a body 302 having at least two ears and a receptacle therebetween which can be positioned about or around a bony structure to provide support and also secure implant 300 thereto.

For example, in FIG. 14 implant 300 includes ears formed by a first portion 304 and a second portion 306. A first engaging surface 308 extends between first portion 304 and second portion 306. Body 302 further includes a second pair of ears formed by a third portion 310 and a fourth portion 312. A second engaging surface 314 extends between third portion 310 and fourth portion 312. Body 302 includes a first outer surface 316 along first and third portions 304, 310, and a second outer surface 318 along second and fourth portions 306, 312. A third outer surface 320 extends between first and second portion 304, 306 and third and fourth portion 310, 312 along one side of body 302, and fourth outer surface 322 is opposite third outer surface 320.

In one embodiment, it is contemplated that implant 300 is provided with a flexible body 302 that compresses when the adjacent bony portions supported thereby move toward one another and returns towards it relaxed, uncompressed state as the adjacent bony portions supported thereby move away from one another. It is further contemplated that implant 300 can be made of any bio-compatible material, including synthetic or natural autograft, allograft or xenograft tissues, and can be resorbable or non-resorbable in nature. Examples of tissue materials include hard tissues, connective tissues, demineralized bone matrix and combinations thereof. Further examples of resorbable materials are polylactide, polyglycolide, tyrosine-derived polycarbonate, polyanhydride, polyorthoester, polyphosphazene, calcium phosphate, hydroxyapatite, bioactive glass, and combinations thereof. Further examples of non-resorbable materials are non-reinforced polymers, carbon-reinforced polymer composites, PEEK and PEEK composites, shape-memory alloys, titanium, titanium alloys, cobalt chrome alloys, stainless steel, ceramics and combinations thereof and others as well.

Figure 15:
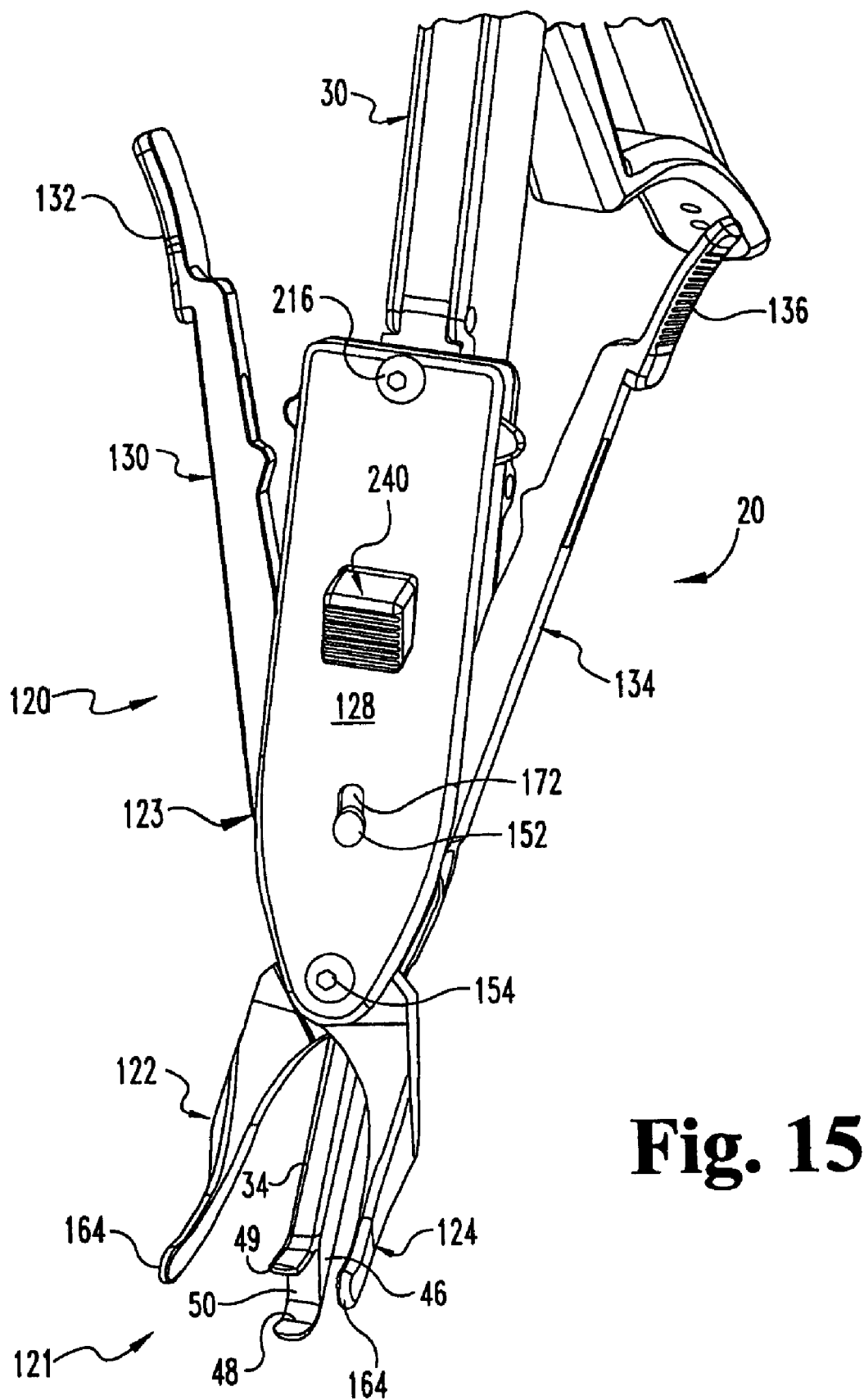
FIG. 15 is a perspective view of a distal portion of the implant inserter of FIG. 1 in a release position.

In FIG. 15, engaging portion 121 and clamp assembly 120 of inserter instrument 20 are shown with clamping members 122, 124 separated from one another with lever arms 130, 134 to facilitate placement of an implant, such as implant 300, therebetween. In FIG. 16, implant 300 is shown prior to placement on holder 46 and prior to clamping members 122, 124 being moved to their clamping position. Implant 300 is oriented so that first outer surface 316 is positioned along the portion of cradle surface 50 between holder extensions 48, 49, and so that first extension 48 extends along fourth outer surface 322 and second extension 49 extends along third outer surface 320. Cradle surface 50 can provide at least some frictional engagement with implant 300 to maintain it in holder 46 before, during and after insertion.

Figure 17:
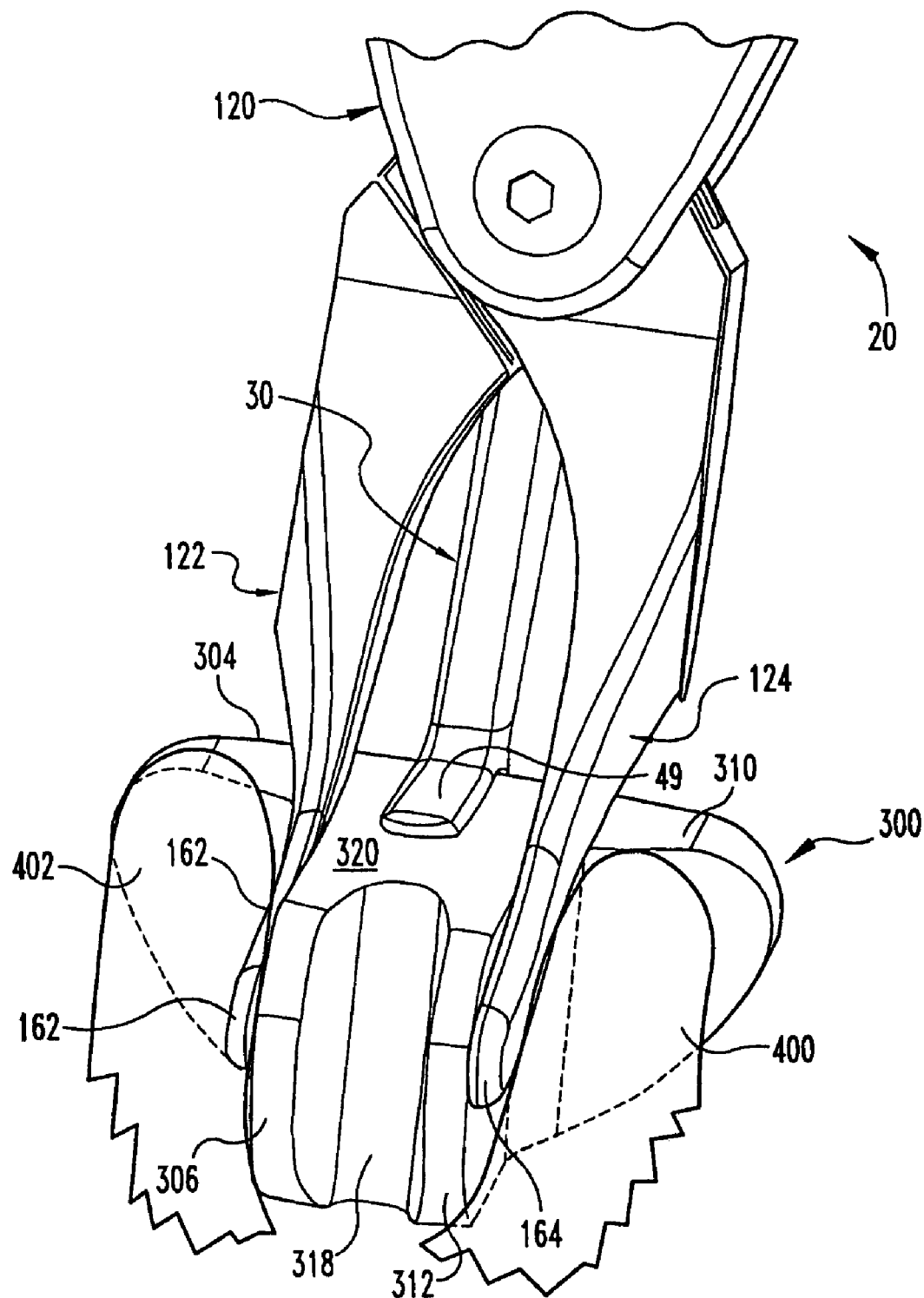
FIG. 17 is a perspective view of a distal portion of the implant inserter of FIG. 1 engaged with the implant of FIG. 14 and with the implant positioned between adjacent bony portions.

In the illustrated embodiment, implant 300 is made from a compressible and resilient material. Implant 300 is positioned in holder 46, and second portion 306 and third portion 314 can be manually squeezed together if necessary for placement between the opened clamping members 122, 124. In FIG. 17, clamping members 122, 124 have been moved toward one another after placement of implant 300 therebetween by pivoting lever arms 130, 134 toward longitudinal axis 23. Distal arm portions 162, 164 of clamping members 122, 124 clamp against at least second portion 306 and fourth portion 312 of implant 300, further compressing them between clamping members 122, 124 to a reduced size configuration. Clamping members 122, 124 can further compress body 302 of implant 300 between engaging surfaces 308, 314. Second portion 306 and fourth portion 312 flex distally when compressed in substantial alignment with the adjacent engaging surface 308, 314.

Figure 18:
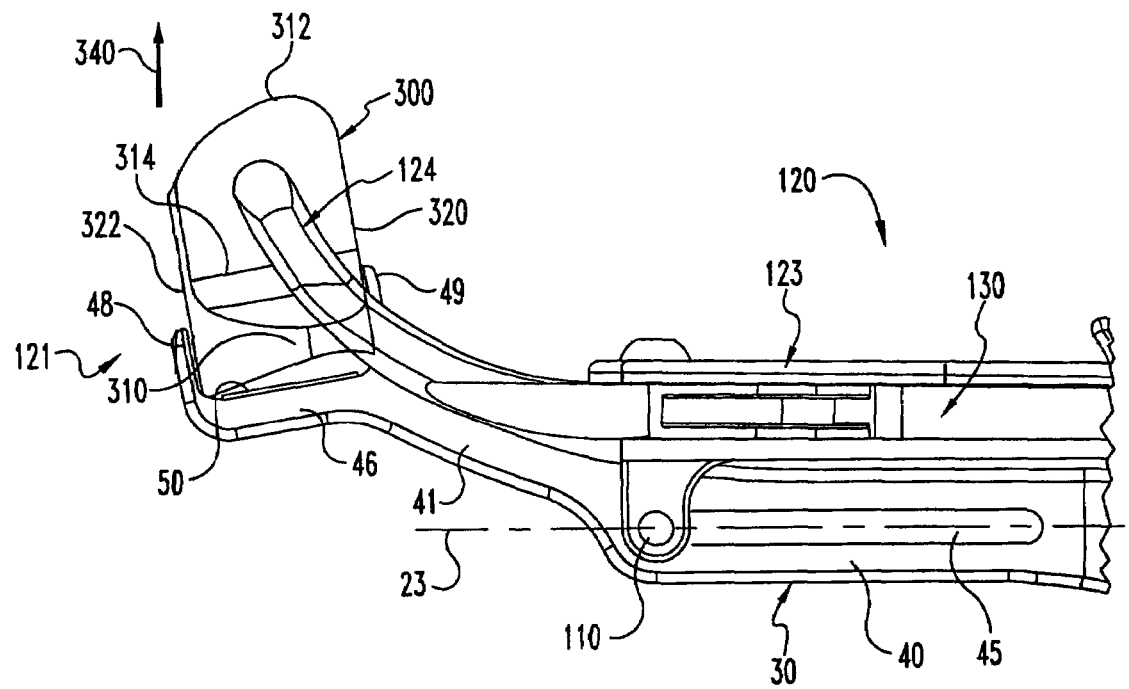
FIG. 18 is a side elevational view of a distal portion of the implant inserter of FIG. 1 in an engaged position with the implant of FIG. 14.

In this clamped and compressed condition, implant 300 is inserted in the space between adjacent spinous processes 400, 402, as shown in FIG. 17. Portions 306, 312 and body 302 are compressed sufficiently for implant 300 and clamping members 122, 124 to be positioned through the interspace between the spinous processes from a lateral approach offset from the spinal midline in a direction indicated by arrow 340 in FIG. 18. Holder 46 remains offset to the near lateral side of the interspinous space.

Figure 19:
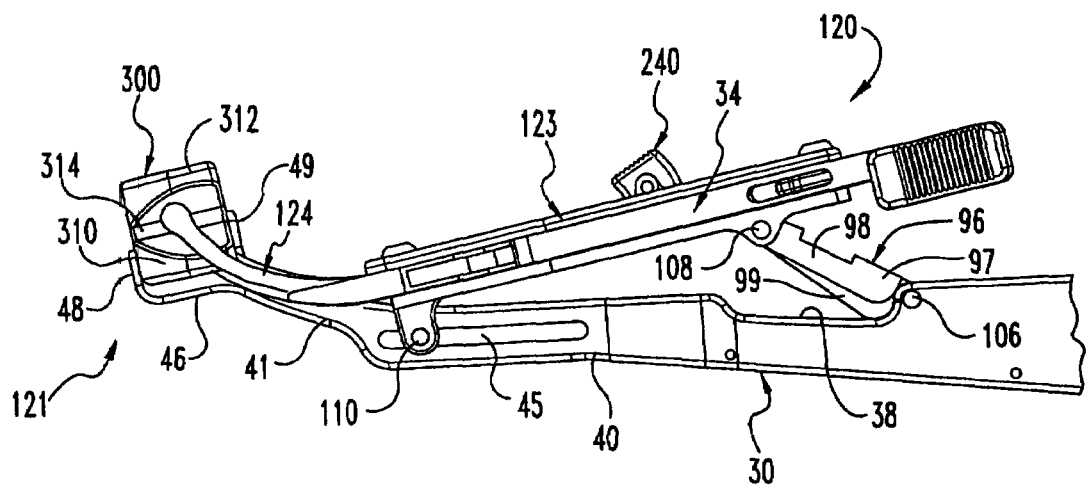
FIG. 19 is a side elevational view of a distal portion of the implant inserter of FIG. 1 as the clamping members are being released from the implant of FIG. 14.

With the implant initially positioned between the spinous processes, lock button 240 can be pressed to allow lever arms 130, 134 to be pivoted to at least partially release the clamping force applied by clamping members 122, 124. As shown in FIG. 19, handle assembly 22 has been manipulated to actuate actuating assembly 125 and begin deployment of clamp assembly 120. Release of the clamping force on implant 300 with clamping members 122, 124 can facilitate withdrawal of clamping members 122, 124 from the interspinous space. As clamping members 122, 124 are withdrawn proximally along implant 300, implant 300 is further seated into cradle 46, which maintains the positioning of implant 300 in the interspinous space as clamp assembly 120 is deployed.

In FIG. 20, clamp assembly 120 has been completely deployed so that clamping members 122, 124 are in a low profile orientation along longitudinal axis 23. As clamping members 122, 124 are disengaged with portions 306, 312, portions 306, 312 return toward their relaxed state and extend along a far lateral side of the adjacent spinous processes, while portions 304, 310 extend along the near lateral sides of the adjacent spinous processes. Engaging surfaces 308, 314 extend along the surfaces of the spinous processes oriented toward one another. After deployment of clamp assembly 120 and prior to withdrawal of engaging portion 121 from the approach to the adjacent spinous processes 400, 402, holder 46 can be used to reposition implant 300 in the interspinous space.

Figure 21:
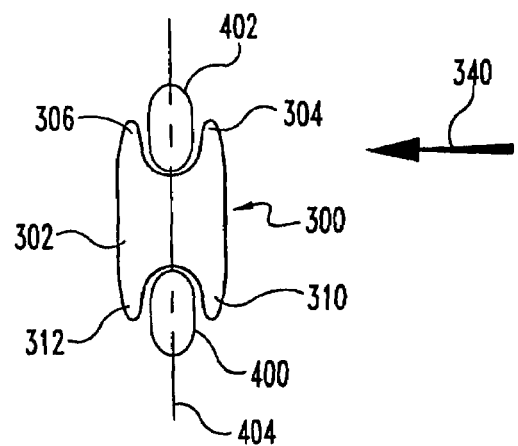
FIG. 21 is an elevational view looking in the anterior direction at the implant of FIG. 14 positioned between adjacent spinous processes.

The final position of implant 300 between spinous processes 400, 402 is shown in FIG. 21. Implant 300 is positioned between spinous processes 400, 402 from an access opening offset to one side of spinal mid-line 404 in an approach indicated by arrow 340. During insertion, second and fourth portions 306, 312 of implant 300 are compressed to fit through the space between spinous processes 400, 402 at midline 404. When clamping members 122, 124 are removed, the compressed second and fourth portions 306, 312 return toward their pre-compressed state and extend axially along the adjacent spinous processes 400, 402, securing implant 300 therebetween. Inserter instrument 20 does not require a second access opening for insertion of an instrument or tool opposite the access opening created for insertion of implant 300 to pull, guide and/or compress the implant as it is positioned between spinous processes 400, 402.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A surgical instrument for inserting an implant, comprising:
    a handle assembly at a proximal end of the instrument;
    an actuator assembly extending along a longitudinal axis and operably coupled with said handle assembly, and
    an implant engaging portion at a distal end of the instrument, said implant engaging portion including a holder positionable in contact with the implant and a clamp assembly coupled with said actuator assembly, said clamp assembly including a pair of distal arm portions adjacent said holder and movable toward one another to engage the implant between said distal arm portions, said distal arm portions further being movable proximally relative to said holder with said actuator assembly upon manipulation of said handle assembly to release the implant from between said distal arm portions while said holder maintains contact with the implant.

2. The instrument of claim 1, wherein said holder includes first and second extensions and a cradle surface extending along and between said first and second extensions, the implant being positionable between said first and second extensions in contact with said cradle surface.

3. The instrument of claim 1, wherein said holder is aligned between said distal arm portions.

4. The instrument of claim 1 wherein said distal arm portions each include a distal end and are curved along the longitudinal axis to offset said distal ends to a first side of the longitudinal axis.

5. The instrument of claim 4, wherein said holder is positioned at a distal end of a holder arm, said holder arm extending along the longitudinal axis and including a curved distal portion to offset said holder to the first side of the longitudinal axis.

6. The instrument of claim 5, wherein said holder includes first and second extensions and a cradle surface extending along and between said first and second extensions, the implant being positionable between said first and second extensions in contact with said cradle surface, wherein said first and second extensions extend transversely to the longitudinal axis.

7. The instrument of claim 6, wherein said handle assembly includes first and second handle members transversely oriented to the longitudinal axis and extending therefrom in a direction opposite the first side.

8. The instrument of claim 1, wherein said handle assembly includes a first handle member and a second handle member pivotally coupled to said first handle member.

9. The instrument of claim 8, wherein:
    said handle assembly includes a holder arm extending distally from said first handle member along the longitudinal axis, said holder arm including said holder at a distal end thereof; and
    said actuator assembly is operably coupled with said second handle member.

10. The instrument of claim 9, wherein:
    said clamp assembly extends between a proximal end and a distal end and includes a pair of clamping members, said distal arm portions comprise a distal portion of said pair of clamping members and extend distally from said clamp assembly, wherein:
    said proximal end of said clamp assembly is coupled to said actuating assembly;
    said distal end of said clamp assembly is coupled to said holder arm; and
    movement of said second handle member relative to said first handle member actuates said actuating assembly and translates said clamp assembly and said distal portions of said pair of clamping members along said holder arm.

11. The instrument of claim 10, further comprising a spring mechanism between said first and second handle members, wherein said spring mechanism normally biases said handle assembly in a first orientation wherein said clamp assembly is distally positioned relative to said holder arm, and movement of said second handle member toward said first handle member translates said clamp assembly and said distal portions of said clamping arms proximally along said holder arm.

12. The instrument of claim 10, wherein said actuating assembly includes:
a link member extending between a distal end and a proximal end, said proximal end of said link member being pivotally coupled to said second handle member; and
a crank member including a rotational center pivotally coupled to said holder arm, a proximal pivot end pivotally coupled to said distal end of said link member, and a distal pivot end pivotally coupled to said proximal end of said clamp assembly.

13. The instrument of claim 12, wherein in an undeployed position of said clamp assembly said proximal end of said clamp assembly is positioned adjacent the longitudinal axis and in a deployed position of said clamp assembly said crank member is rotated about said rotational center with said link member acting on said proximal pivot end to move said distal pivot end and said proximal end of said clamp assembly proximally and away from the longitudinal axis.

14. The instrument of claim 1, wherein said clamp assembly extends between a proximal end and a distal end and said distal arm portions extend distally from said distal end, said actuating assembly being coupled to said proximal end of said clamp assembly; and further comprising:
a bolder arm extending distally from said handle assembly along the longitudinal axis, said holder being at a distal end of said holder arm and said distal end of said clamp assembly being coupled with said holder arm, wherein said clamp assembly and said distal arm portions are movable along said holder arm by actuating said actuating assembly.

15. The instrument of claim 14, wherein said clamp assembly includes a first lever arm coupled with a first one of a pair of clamping members and a second lever arm coupled with a second one of a pair of clamping members, said distal arm portions comprising a distal portion of respective ones of said clamping members, said first and second lever arms being pivotally coupled to one another and movable relative to one another to displace said distal arm portions of said pair of clamping members toward one another to a clamping position and to displace said distal arm portion of said pair of clamping members away from one another to a release position.

16. The instrument of claim 15, wherein said clamp assembly includes a lever locking assembly releasably engageable to said lever arms to maintain a positioning between said distal arm portions of said pair of clamping members.

17. The instrument of claim 16, wherein said lever locking assembly includes a lock member and a lock button pivotally coupled to said lock member, said lock member including first and second locking arms extending therefrom and releasably engageable with an adjacent one of said first and second lever arms.

18. The instrument of claim 17, wherein said lock member is normally biased into engagement with said first and second lever arms, and is movable out of engagement with said first and second lever arms by depressing said lock button.

19. The instrument of claim 16, wherein said clamp assembly includes a housing, said lever locking assembly and said first and second lever arms being at least partially contained within said housing.

20. The instrument of claim 19, wherein said housing includes an upper plate and a lower plate, said upper plate being coupled to said lower plate and said lower plate being coupled at a distal end thereof to said holder arm and at a proximal end thereof to said actuating assembly.

21. A surgical instrument for inserting an implant, comprising:
a handle assembly;
a clamp assembly extending from said handle assembly along a longitudinal axis, said clamp assembly including a pair of distal arm portions to engage the implant therebetween; and
an implant engaging portion at a distal end of the instrument, said implant engaging portion including a holder positionable in contact with the implant and said pair of distal arm portions adjacent said holder, said distal arm portions being movable relative to one another to engage the implant therebetween with said holder in contact with the implant, wherein said holder and said distal arm portions are each offset to a first side of the longitudinal axis.

22. The instrument of claim 21, wherein said handle assembly includes first and second handle members transversely oriented to the longitudinal axis.

23. The instrument of claim 22, wherein said first and second handle members extend from the longitudinal axis in a direction opposite the first side of the longitudinal axis.

24. The instrument of claim 21, further comprising an actuator assembly operably coupled between said clamp assembly and said handle assembly, said actuator assembly being manipulatable with said handle assembly to proximally translate said distal arm portions away from said holder.

25. The instrument of claim 21, further comprising an actuator assembly operably coupled between said clamp assembly and said handle assembly, said actuator assembly being manipulatable with said handle assembly to translate said distal arm portions toward said longitudinal axis.

26. The instrument of claim 21, further comprising an actuator assembly operably coupled between said clamp assembly and said handle assembly, said actuator assembly being manipulatable with said handle assembly to proximally translate said distal arm portions proximally away from said holder and toward said longitudinal axis.

27. The instrument of claim 26, wherein said holder is at a distal end of a stationary holder arm extending between said handle assembly and said holder.

28. The instrument of claim 27, wherein said actuator assembly includes:
a link member extending between a proximal end and a distal end, said proximal end being pivotally coupled with said handle assembly; and
a crank member pivotally coupled at an axially fixed rotational center to said holder arm, said crank member further being pivotally coupled at a proximal pivot end thereof with said link member and being pivotally coupled at a distal pivot end of said crank member with said clamping assembly.

29. The instrument of claim 28, wherein said clamp assembly includes a pair of clamping members and a housing, said distal arm portions comprising a distal portion of respective ones of said pair of clamping members, said distal arm portions extending distally from said housing.

30. The instrument of claim 29, wherein a proximal end of said housing is coupled to said distal pivot end of said crank member and a distal end of said housing is pivotally coupled to a slot in said holder arm, said slot being elongated along the longitudinal axis.

31. The instrument of claim 29, wherein said clamp assembly includes first and second lever arms pivotally coupled to said housing and to respective ones of said pair of clamping members, said lever arms being pivotal to move said distal arm portions of clamping members toward one another to clamp an implant therebetween.

32. A surgical instrument for inserting an implant, comprising:
a handle assembly at a proximal end of the instrument;
an actuator assembly extending along a longitudinal axis, and
an implant engaging portion at a distal end of the instrument said implant engaging portion including a holder positionable in contact with the implant and a clamp assembly, said clamp assembly including a pair of distal arm portions adjacent said holder and movable toward one another to engage the implant between said distal arm portion, wherein said actuator assembly is operably coupled between said handle assembly and said clamp assembly, said actuator assembly being manipulatable with said handle assembly to simultaneously translate said distal arm portions away from said holder and toward said longitudinal axis.

33. The instrument of claim 32, wherein said holder is positioned between said distal arm portions.

34. The instrument of claim 32, wherein said distal arm portions are curved along the longitudinal axis such that distal ends of said distal arm portions are offset to a first side of the longitudinal axis.

35. The instrument of claim 34, wherein said holder is positioned at a distal end of a holder arm, said holder arm extending along the longitudinal axis and including a curved distal portion to offset the holder member to the first side of the longitudinal axis.

36. The instrument of claim 32, wherein said holder includes first and second extensions and a cradle surface extending along and between said first and second extensions, the implant being positionable between said first and second extensions in contact with said cradle surface.

37. The instrument of claim 32, wherein said handle assembly includes first and second handle members transversely oriented to the longitudinal axis.

38. The instrument of claim 32, wherein handle assembly includes a first handle member coupled to a second handle member.

39. The instrument of claim 38, wherein said handle assembly further includes a holder arm extending distally from said first handle member, said holder arm including said holder at a distal end thereof.

40. The instrument of claim 32, wherein said clamp assembly extends between a proximal end and a distal end, said distal arm portions extending distally from said distal end, said distal end of said clamp assembly being pivotally coupled in a slot in said holder arm and said proximal end of said clamp assembly being pivotally coupled to said actuator assembly.

41. The instrument of claim 40, wherein said clamp assembly includes a first lever arm coupled with a first one of a pair of clamping members and a second lever arm coupled with a second one of said pair of clamping members, said distal arm positions comprising a distal portion of respective ones of said pair of clamping members, said first and second lever arms being pivotally coupled to one another and movable to position said distal arm portions of said pair of clamping members adjacent one another in a clamping position and to position said distal arm portions of said pair of clamping members away from one another to a release position.

42. The instrument of claim 41, wherein said clamp assembly includes a lever locking assembly releasably engageable to said lever arms to maintain a relative position between said pair of clamping members.

43. The instrument of claim 42, wherein said lever locking assembly includes a lock member and a lock button pivotally coupled to said lock member, said lock member including first and second locking arms extending therefrom and releasably engageable with an adjacent one of said first and second lever arms.

44. A surgical instrument for inserting an implant, comprising:
a handle assembly at a proximal end of the instrument;
an implant engaging portion at a distal end of the instrument, the instrument extending along a longitudinal axis between its proximal and distal ends, said implant engaging portion including a holder positionable in contact wit the implant and a pair of distal arm portions adjacent said holder, said pair of distal arm portions movable toward one another to engage the implant therebetween; and
means for coupling said handle assembly with said implant engaging portion, said means being operable with said handle assembly to translate said pair of distal arm portions proximally and transversely to the longitudinal axis wherein distal ends of said arms portions are located proximally of said holder.

45. The instrument of claim 44, wherein said distal ends of said distal arm portions are offset to a first side of the longitudinal axis.

46. A surgical instrument for inserting an implant comprising:
a handle assembly at a proximal end of the instrument;
an actuator assembly extending along a longitudinal axis, and an implant engaging portion at a distal end of the instrument said implant engaging portion including a holder positionable in contact with the implant and a clamp assembly, said clamp assembly including a pair of distal arm portions adjacent said holder and movable toward one another to engage the implant between said distal arm portion, wherein said actuator assembly is operably coupled between said handle assembly and said clamp assembly, said actuator assembly being manipulatable with said handle assembly to translate said distal aim portions away from said holder and toward said longitudinal axis, wherein said clamp assembly extends between a proximal end and a distal end, said distal arm portions extending distally from said distal end, said distal end of said clamp assembly being pivotally coupled in a slot in said holder arm and said proximal end of said clamp assembly being pivotally coupled to said actuator assembly.

47. The instrument of claim 46, wherein said clamp assembly includes a first lever arm coupled with a first one of a pair of clamping members and a second lever arm coupled with a second one of said pair of clamping members, said distal arm portions comprising a distal portion of respective ones of said pair of clamping members, said first and second lever arms being pivotally coupled to one another and movable to position said distal arm portions of said pair of clamping members adjacent one another in a clamping position and to position said distal arm portions of said pair of clamping members away from one another to a release position.

48. The instrument of claim 47, wherein said clamp assembly includes a lever locking assembly releasably engageable to said lever arms to maintain a relative position between said pair of clamping members.

49. The instrument of claim 48, wherein said lever locking assembly includes a lock member and a lock button pivotally coupled to said lock member, said lock member including first and second locking arms extending therefrom and releasably engageable with an adjacent one of said first and second lever arms.

* * * * *